(12) United States Patent
Vézina et al.

(10) Patent No.: US 7,125,978 B1
(45) Date of Patent: Oct. 24, 2006

(54) PROMOTER FOR REGULATING EXPRESSION OF FOREIGN GENES

(75) Inventors: Louis-Philippe Vézina, Neuville (CA); Marc-André D'Aoust, Québec (CA)

(73) Assignee: Medicago Inc., Quebec (CA)

( * ) Notice: Subject to any disclaimer, the term of this patent is extended or adjusted under 35 U.S.C. 154(b) by 164 days.

(21) Appl. No.: 09/678,303

(22) Filed: Oct. 3, 2000

Related U.S. Application Data

(60) Provisional application No. 60/157,129, filed on Oct. 4, 1999.

(51) Int. Cl.
  C12N 15/00 (2006.01)
  C07H 21/02 (2006.01)
  A01H 1/00 (2006.01)

(52) U.S. Cl. ............ 536/24.1; 536/23.1; 536/24.3; 536/24.31; 536/24.32; 536/24.33; 435/320.1; 800/278

(58) Field of Classification Search ............... 536/23.1, 536/24.1, 24.3, 24.31, 24.32, 24.33; 435/320.1; 800/278
See application file for complete search history.

(56) References Cited

U.S. PATENT DOCUMENTS 4,962,028 A  10/1990 Bedbrook et al.
5,110,732 A   5/1992 Benfey et al.

FOREIGN PATENT DOCUMENTS

WO   WO 01/25455    10/1999
WO   WO 0056906      9/2000

OTHER PUBLICATIONS

Last D.I. et al., "Plastocyanin is encoded by a single-copy gene in the pea haploid genome" Plant Molecular Biology, vol. 12, 1989, pp. 655-666.
Keng-Hock Pwee et al. "The pea plastocyanin promoter directs call-specific but not full light-regulated expression in transgenic tobacco plants" The Plant Journal, G.B. Blackwell Scientific Publications, Oxford, vol. 3, No. 3, 1993, pp. 437-449.
Jefferson R.A. et al. "GUS fusions B-glucuronidase as a sensitive and versatile gene fusion marker in higher plants" The EMBO Journal, 1987, 6(13): 3901-3907.
Darveau A. et al. "PCR-mediated synthesis of chemeric molecules" Methods in Neurosciences, 1995, 26: 77-85.
Khoudi H. et al. "Production of a diagnostic monoclonal antibody in perennial alfalfa plants" Biotechnology and Bioengineering, 1999, 64(2): 135-143.
Atanassov A. & Brown D.C.W. "Plant regeneration from suspension culture and mesophyll protoplasts", Medicago Sativa L. Plant cell tissue and organ culture, 1984, 3: 149-162.
Murashige T. & Skoog F. "A revised medium for rapid growth and bioassays with tobacco tissue cultures" Physiologia Plantarum, 1962 15: 473-497.
Desgagnes et al. "Genetic transformation of commercial breeding lines of alfalfa (Medicago sativa)", Plant Cell tissue Organ Culture, 1995, 42: 129-140.
Sanger et al. "DNA sequencing with chain-terminating inhibitors", P.N.A.S. USA 1977, 74: 5643-5647.
Oommenn et al. "The Llicitor-Inducible Alfalfa Isoflavone Reductase Promoter Confers Different Patterns of Developmental Expression in Homologous and Heterologous Transgenis Plants" The Plant Cell 1994, vol. 6: 1789-1803.
Back et al., "Isolation of the spinach nitrite reductase gene promoter which confers nitrate inducibility on GUS gene expression in transgenic tobacco", Plant molecular biology, 1991, 17: 9-18.
Sander et al., "Structure and expression of a nitrite reductase gene from bean *(Phaseolus Vulgaris) and promoter analysis in transgenic tobacco*" Plant molecular biology, 1995, 27: 165-177.
De Vries et al. 1988, "Isolation of total and polysomal RNA from plant tissue", *Plant Molecular Biology Manual*, Dordrecht: Kluwer Academic Publisher, 1988, B6 pp. 1-13.

*Primary Examiner*—Cynthia Collins
*Assistant Examiner*—Georgia Helmer
(74) *Attorney, Agent, or Firm*—Ogilvy Renault, LLP

(57) ABSTRACT

The present invention relates to a promoter for regulating expression of foreign genes in transgenic organisms, which comprises a promoter having the identifying characteristics of a promoter having a sequence selected from the group consisting of sequences set forth in SEQ ID NOS:1 to 3 and functional fragments or derivatives thereof, wherein said promoter is adapted to be operationally located with respect to said foreign gene for expression of said gene.

3 Claims, No Drawings

PROMOTER FOR REGULATING EXPRESSION OF FOREIGN GENES

This application claims benefit of Provisional Application No. 60/157,129 filed Oct. 4, 1999.

BACKGROUND OF THE INVENTION (a) Field of the Invention

The invention relates to a promoter for regulating expression of foreign genes in a transgenic organism, more specifically in a leaf-specific manner in transgenic plants.

(b) Description of Prior Art

Genetic transformation of microbes have been used for more than 15 years to produce useful recombinant molecules, and applications in the pharmaceutical, cosmaceutical and dermaceutical industries are being currently exploited. This technology has expanded from microbes to plants and animals in the last ten years with the development of techniques required to adapt this general concept to complex eukaryotic organisms. Basically a gene encoding for a protein of interest or a gene encoding for an enzyme responsible for a modification of a metabolic pathway that leads to a molecule of interest, is linked in an appropriate fashion to cis- and trans-acting regulatory sequences, and transferred to a target cell where it is incorporated in the molecular machinery (in a transitory or stable fashion). The transgenic cell, or a tissue or organism regenerated from the transgenic cell will then perform transcription and translation of the transgene and therefore be enabled to accumulate the protein of interest or to perform the new metabolic reaction through the activity of the enzyme of interest.

The emerging industry of molecular farming is one of the most promising industry of the coming century. Its promise is to provide safe and renewable molecule factories for the industry. Among the applications that are currently developed are the production of low-cost monoclonal antibodies for therapeutic and diagnostic uses, the production of unlimited amounts of hormones, cytokines and other bio-active molecules for the treatment of chronicle or lethal diseases, the production of bio-safe substitutes for various blood components, the production of unlimited amounts of processing enzymes for the food and pulp industry, the production of low-cost enzymes for waste treatments, and the production of safe bio-active molecules for the cosmetic industry.

Limitations to the application of this technology has often come from the inability of transgenic organisms to accumulate adequate amounts of the recombinant product, as a result of low transcription rates, improper splicing of the messenger, instability of the foreign mRNA, poor translation rates, hyper-susceptibility of the recombinant protein to the action of endogenous proteases or hyper-susceptibility of the recombinant organism to the foreign protein which result in improper and limited growth or in the worst cases, in strong deleterious effects to the host organism. Inadequacy of production level has a direct impact on the development of applications when profit margins are narrow, or when treatment and/or disposal of residual matter causes bio-safety or environmental problems. Improvement of the accumulation level of the desired recombinant product thus appears to be one critical factor that warrants commercialization of many applications of molecular farming.

Photosynthesis is a metabolic reaction of paramount importance in the living world. It is performed by most land plants and algae, and by some bacteria. This overall reaction involves a complex assembly of electron transfer proteins spatially arranged within the thylakoid membrane system located in the chloroplast of leaf cells. This electron transport chain is coupled at one end with the photosynthetic antennae, which comprise a variety of macro-molecules, including one molecule common to all photosynthetic organism, chlorophyll, and at the other end, to the enzymes involved in NADPH and ATP synthesis, and to the Calvin cycle, involved in coupling the release of energy from NADPH and ATP with the fixation of gaseous carbon dioxide into organic molecules. Among the proteins involved in the overall photosynthetic reaction, one, Ribulose biphosphate carboxylase (Rubisco), is the most abundant protein on earth.

Photosynthesis is thus what leaf cells are dedicated to perform, and there is an obvious interest to use promoters of genes involved in such prominent tissue-specific metabolic activity when building strong leaf-specific expression cassettes for applications in plant biotechnology.

Many of the peptidic constituents of the photosynthetic apparatus are encoded by genes present in the chloroplastic genome; as an example, the heavy subunit of Rubisco, which bears the catalytic sites for $CO_2$ fixation, is encoded by a chloroplastic gene. However, the small subunit of this enzyme is encoded by a nuclear gene, and thus the Rubisco holo-protein is made of subunits encoded by two different genomes. For obvious reasons, there has been a great interest in trying to use Rubisco promoters to control transcription of transgenes in leaves of transgenic plants. The promoter has been extensively characterized and its use in expression vectors is protected by U.S. Pat. No. 4,962,028.

It would be highly desirable to be provided with a promoter for regulating expression of foreign genes in a transgenic organism, more specifically in transgenic plants.

SUMMARY OF THE INVENTION

One aim of the present invention is to provide with a promoter for regulating expression of foreign genes in a transgenic organism, more specifically in transgenic plants.

In accordance with one embodiment of the present invention, there is provided a promoter for regulating expression of foreign genes in transgenic organisms, which comprises a promoter having the identifying characteristics of a promoter having a sequence selected from the group consisting of sequences set forth in SEQ ID NOS:1 to 3 and functional fragments or derivatives thereof, wherein said promoter is adapted to be operationally located with respect to said foreign gene for expression of said gene.

The preferred promoter of the present invention has a sequence selected from the group consisting of sequences set forth in SEQ ID NOS:1 to 3.

Preferably, the organism is a plant.

Preferably, the promoter of the present invention may be modulated by the presence or absence of light.

The prefered plant is a dicot, a monocot or a gymnosperm.

In accordance with another embodiment of the present invention, there is provided a method of regulating expression of foreign genes in transgenic organisms, comprising the steps of:

a) preparing a transgenic organism using an expression construct consisting of at least a promoter of the present invention, and an ORF of a gene, wherein said promoter is operationally located with respect to said gene for expression of said gene.

For the purpose of the present invention the following terms are defined below.

The expression "functional fragments or derivatives thereof" is intended to mean any derivative or fragment of sequences SEQ ID NOS:1–3 which allow for an equivalent level of expression of a foreign gene as the promoter of the present invention set forth in SEQ ID NOS:1–3.

DETAILED DESCRIPTION OF THE INVENTION

Following is a detailed description of the method used to generate transgenic alfalfa lines that can be regulated in their expression of a reporter gene.

In this embodiment, a promoter having the sequence set forth in SEQ ID NOS:1–3 was then ligated to a reporter gene and a terminator, and this construct was inserted in suitable plant expression vectors for DNA bombardment onto alfalfa leaves and for *Agrobacterium* mediated DNA transfer as described by Desgagnés et al. (1995, *Plant Cell Tissue Organ Cult.* 42:129–140). These two DNA transfer methods were used to demonstrate that expression of the reporter gene can be modulated by light.

Materials and Methods

DNA Sequencing

DNA sequencing was performed as described by Sanger et al (1977, *P.N.A.S. USA*, 74:5643–5647).

The resulting promoters of the present invention have the sequence as set forth in SEQ ID NOS: 1 to 3.

Construction of Expression Cassettes and Vectors

The cassettes for expression analysis using the GUS reporter gene were assembled as follows. A promoterless GUS cassette was digested from PBI101 with HindIII and EcoRI, and was inserted into the HindIII and ECORI sites of the pUC19 polycloning site. The resulting plasmid was named pBI201 and was used for further constructs. SEQ ID NO:2 and SEQ ID NO:3, two and deletion fragments of SEQ ID NO:1, were operably fused at the 5' terminus of the GUS reporter gene in pBI201 by PCR ligation, and resulting constructs were used for transitory expression studies using DNA bombardment or subcloned into a binary plant expression vector such as pBI101 (Clonetech). These recombinant plasmids were used for stable integration through *A. tumefaciens* infection as described below.

*Agrobacterium*-mediated DNA transfer and regeneration of transgenic lines

The recombinant plasmids were introduced into *Agrobacterium tumefaciens* strain LBA4404 by electroporation as described in Khoudi et al (1999, *Biotechnol. Bioeng.*, 64:135–143). Selected *Agrobacterium* strains were then co-cultivated with leaf disks from genotype C5-1 for 4 days in the absence of selection pressure (kanamycin). Following this incubation period, leaf disks were washed and pampered, and then allowed to form calli onto medium B5H. Calli were then transferred for 21 days on SH medium for embryo induction and for 28 days on BOi2Y for embryo development. Torpedo-shaped embryos were removed from Boi2Y and placed on MS medium for regeneration. Kanamycin was present in all cultivation medium except for co-cultivation and regeneration on MS. This method is described in length in Desgagnés et al (1995, *Plant Cell Tissue Organ Cult.* 42:129–140). Rooted plantlets were grown to maturity in the greenhouse.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated promoter having a sequence selected from the group consisting of the sequences set forth in SEQ ID NOs: 1 to 3, wherein said promoter is operably linked to a foreign DNA of interest for expression of said foreign DNA of interest.

2. An expression vector comprising a promoter of claim 1.

3. A plant cell or a plant genetically transformed with the expression vector of claim 2.

* * * * *

SEQUENCE LISTING

```
<160> NUMBER OF SEQ ID NOS: 3

<210> SEQ ID NO 1
<211> LENGTH: 1350
<212> TYPE: DNA
<213> ORGANISM: Artificial Sequence
<220> FEATURE:
<223> OTHER INFORMATION: Sequence to be used as a Promoter for
      regulating expression

<400> SEQUENCE: 1
cgacggcccg ggctggtata tttatatgtt gtcaaataac tcaaaaacca taaaagttta      60
agttagcaag tgtgtacatt tttatttgaa caaaaatatt cacctactac tgttataaat     120
cattattaaa cattagagta aagaaatatg gatgataaga acaagagtag tgatattttg     180
acaacaattt tgttgcaaca tttgagaaaa ttttgttgtt ctctcttttc attggtcaaa     240
aacaatagag agagaaaaag gaagagggag aataaaaaca taatgtgagt atgagagaga     300
aagttgtaca aaagttgtac caaaatagtt gtacaaatat cattgaggaa tttgacaaaa     360
gctacacaaa taagggttaa ttgctgtaaa taaataagga tgacgcatta gagagatgta     420
ccattagaga attttttggca agtcattaaa aagaaagaat aaattattttt taaaattaaa    480
```

-continued

```
agttgagtca tttgattaaa catgtgatta tttaatgaat tgatgaaaga gttggattaa    540
agttgtatta gtaattagaa tttggtgtca aatttaattt gacatttgat cttttcctat    600
atattgcccc atagagtcag ttaactcatt tttatatttc atagatcaaa taagagaaat    660
aacggtatat taatccctcc aaaaaaaaaa aacggtatat ttactaaaaa atctaagcca    720
cgtaggagga taacatccaa tccaaccaat cacaacaatc ctgatgagat aacccacttt    780
aagcccacgc actctgtggc acatctacat tatctaaatc acacattctt ccacacatct    840
gagccacaca aaaaccaatc cacatcttta tcacccattc tataaaaaat cacactttgt    900
gagtctacac tttgattccc ttcaaacaca tacaaagaga agagactaat taattaatta    960
atcatcttga gagaaaatgg ccaccgttac ttccaccacc gttgctattc catcattcac   1020
aggccttaag gcaaacgcaa gcaaagttaa tgccatagct aaggttccaa cttcaacttc   1080
tcaattgcca aggctttgtg tcagagcttc cctcaaagac tttggagttg ctgctgttgc   1140
cactgctgca agtgcattgt tagctagcaa tgcccttgca gttgaagtgt tgcttggtgc   1200
tagtgatggg ggtttggctt ttgttccaaa caatttcaca gtgaacgctg gagacaccat   1260
tacattcaag aacaatgctg gttttcctca caacgttatc ttcgatgaag acgagattcc   1320
aagcggggtt gatgctgcaa tcgaattccc                                   1350
```

<210> SEQ ID NO 2
<211> LENGTH: 971
<212> TYPE: DNA
<213> ORGANISM: Artificial Sequence
<220> FEATURE:
<223> OTHER INFORMATION: Sequence to be used as a Promoter for
      regulating expression

<400> SEQUENCE: 2

```
cgggctggta tatttatatg ttgtcaaata actcaaaaac cataaaagtt taagttagca     60
agtgtgtaca tttttattg aacaaaaata ttcacctact actgttataa atcattatta    120
aacattagag taaagaaata tggatgataa gaacaagagt agtgatattt tgacaacaat    180
tttgttgcaa catttgagaa aattttgttg ttctctcttt tcattggtca aaacaatag    240
agagagaaaa aggaagaggg agaataaaaa cataatgtga gtatgagaga gaaagttgta    300
caaaagttgt accaaaatag ttgtacaaat atcattgagg aatttgacaa aagctacaca    360
aataagggtt aattgctgta aataaataag gatgacgcat tagagagatg taccattaga    420
gaattttgg caagtcatta aaaagaaaga ataaattatt tttaaaatta aaagttgagt    480
catttgatta aacatgtgat tatttaatga attgatgaaa gagttggatt aaagttgtat    540
tagtaattag aatttggtgt caaatttaat ttgacatttg atcttttcct atatattgcc    600
ccatagagtc agttaactca tttttatatt tcatagatca aataagagaa ataacggtat    660
attaatccct ccaaaaaaaa aaaacggtat atttactaaa aaatctaagc cacgtaggag    720
gataacatcc aatccaacca atcacaacaa tcctgatgag ataacccact ttaagcccac    780
gcactctgtg gcacatctac attatctaaa tcacacattc ttccacacat ctgagccaca    840
caaaaaccaa tccacatctt tatcacccat tctataaaaa atcacacttt gtgagtctac    900
actttgattc ccttcaaaca catacaaaga agagactaa attaattaat taatcatctt    960
gagagaaaat g                                                       971
```

<210> SEQ ID NO 3
<211> LENGTH: 731
<212> TYPE: DNA

-continued

```
<213> ORGANISM: Artificial Sequence
<220> FEATURE:
<223> OTHER INFORMATION: Sequence to be used as a Promoter for
      regulating expression

<400> SEQUENCE: 3
agagagaaaa aggaagaggg agaataaaaa cataatgtga gtatgagaga gaaagttgta    60
caaaagttgt accaaaatag ttgtacaaat atcattgagg aatttgacaa aagctacaca   120
aataagggtt aattgctgta aataaataag gatgacgcat tagagagatg taccattaga   180 gaattttgg caagtcatta aaagaaaga ataaattatt tttaaaatta aaagttgagt    240
catttgatta aacatgtgat tatttaatga attgatgaaa gagttggatt aaagttgtat   300
tagtaattag aatttggtgt caaatttaat ttgacatttg atcttttcct atatattgcc   360
ccatagagtc agttaactca tttttatatt tcatagatca aataagagaa ataacggtat   420
attaatccct ccaaaaaaaa aaaacggtat atttactaaa aaatctaagc cacgtaggag   480
gataacatcc aatccaacca atcacaacaa tcctgatgag ataacccact ttaagcccac   540
gcactctgtg gcacatctac attatctaaa tcacacattc ttccacacat ctgagccaca   600
caaaaaccaa tccacatctt tatcacccat tctataaaaa atcacactt gtgagtctac    660 actttgattc ccttcaaaca catacaaaga gaagagacta attaattaat taatcatctt   720
gagagaaaat g                                                        731
```